United States Patent [19]

Wolfer

[11] Patent Number: 5,031,639
[45] Date of Patent: Jul. 16, 1991

[54] BODY CUFF

[76] Inventor: Joseph A. Wolfer, 4903 W. Carol Ave., Glendale, Ariz. 85302

[21] Appl. No.: 485,634

[22] Filed: Feb. 27, 1990

Related U.S. Application Data

[63] Continuation-in-part of Ser. No. 270,083, Nov. 14, 1988, Pat. No. 4,949,679.

[51] Int. Cl.$^5$ .............................................. A61F 5/37
[52] U.S. Cl. ................................... 128/874; 128/875; 128/873; 128/869
[58] Field of Search .......................... 128/869, 873–876

[56] References Cited

U.S. PATENT DOCUMENTS

| | | | |
|---|---|---|---|
| 2,664,083 | 12/1953 | Heymans | 128/873 |
| 2,948,278 | 8/1960 | Topa | 128/873 |
| 3,361,132 | 1/1968 | Rentsch, Jr. | 128/873 |
| 3,399,670 | 9/1968 | Veasey | 128/876 X |
| 4,172,453 | 10/1979 | Leckie | 628/876 X |
| 4,852,587 | 8/1989 | Share | 128/873 X |
| 4,860,360 | 8/1989 | Lundelius | 128/876 X |

Primary Examiner—Mickey Yu
Assistant Examiner—Brian E. Hanlon
Attorney, Agent, or Firm—Tod R. Nissel

[57] ABSTRACT

Apparatus for maintaining the wrists and hands of an individual adjacent the individual's waist.

15 Claims, 4 Drawing Sheets

BODY CUFF

This is a continuation in part of application Ser. No. 270,083, filed Nov. 14, 1988, for "APPARATUS FOR SECURING AN INDIVIDUAL'S HANDS ADJACENT HIS WAIST", now U.S. Pat. No. 4,949,679.

This invention pertains to apparatus for restraining and controlling the movements of an individual.

More particularly, the invention pertains to a method and apparatus for seating an individual in a vehicle with his wrists handcuffed behind his back, the method preventing the individual from working his hands under his buttocks and legs to the front of his body.

In a further respect, the invention pertains to a method and apparatus for walking an individual to a vehicle and seating the individual in the vehicle, the method and apparatus minimizing the likelihood that the individual can escape from or injure a police officer or other person escorting the individual to the vehicle.

Apparatus for restraining an individual being transported in a vehicle is well known in the art. See, for example, U. S. Pat. Nos. 1,823,697 to Nenstiehl and 3,007,331 to Irwin. Such prior art apparatus has important disadvantages. These disadvantages are probably why such apparatus is apparently not utilized by various law enforcement agencies in the United States. In particular, in the Nenstiehl and Irwin references, the suspect's hands are cuffed in front of the individual. A police officer must put his head, hands and arms inside the vehicle to attach the securing strap or member to the suspect's handcuffs. The officer must do the same when the individual is being removed from the vehicle. When the officer's head, arms and hands are inside the vehicle, the officer is vulnerable to being kicked in the head by the suspect's knees or to being struck by the individual's wrists and handcuffs.

Another disadvantage of conventional handcuffing procedures is that a handcuffed individual is normally walked to the officer's car with the officer behind the individual and holding on to his belt. A suspect can often break the officer's hold on his belt and turn and strike the officer or turn and run from the officer.

Finally, since the apparatus described in the earlier mentioned Irwin and Nenstiehl patents is not utilized in present day police vehicles, suspects are placed in the back seat of the car with their hands cuffed behind the back. After the vehicle door is closed and the officer is driving the vehicle to a desired location, the suspect can sometimes work his hands underneath the buttocks and legs to the front of his body. When the officer opens the door of the vehicle to remove the suspect, the suspect is better able to kick the officer or strike him with his handcuffs.

The importance of the afore-mentioned disadvantages in conventional procedures for securing an individual while in a vehicle and while the individual is walked to the vehicle is demonstrated by the fact that handcuffed suspects have managed to knock police officers down and take their gun, with dire consequences.

Accordingly, it would be highly desirable to provide an improved method and apparatus for walking a handcuffed individual to a vehicle and securing him in the vehicle so the individual cannot work his hands beneath his buttocks and legs to the front of his body.

It would also be highly desirable to provide an improved method and apparatus for walking a handcuffed individual to a vehicle, the method increasing the ability of an officer to control the individual and prevent the individual from escaping or injuring the officer.

Therefore, it is a principal object of the invention to provide an improved method and apparatus for controlling and restraining an individual when the individual is walked to a vehicle and secured therein.

Another object of the instant invention is to provide an improved method and apparatus for controlling an individual which reduces the likelihood a suspect can escape from a police officer, in particular a female officer, while the suspect is being walked to a vehicle.

A further object of the invention is to provide an improved method and apparatus for controlling a handcuffed individual while the individual is escorted by a police officer to a vehicle.

These and other and further and more specific objects and advantages of the invention will be apparent to those skilled in the art from the following detailed description thereof, taken in conjunction with the drawings, in which:

FIG. 11 is a partial bottom view of the body cuff assembly of FIG. 10;

FIG. 12 is a front view of an individual wearing the body cuff assembly of FIG. 10; and, FIG. 13 is a rear view of an individual wearing the body cuff assembly of FIG. 10.

Briefly, in accordance with my invention, I provide a method for securing an individual in the seat of a vehicle, the seat including an upstanding backing and a horizontally oriented support member having a rear portion and a front portion. The method includes the steps of attaching handcuffs to the wrists of an individual's hands behind his back; attaching to the handcuffs a first pliable control strap having a first end with latching means and a second end with a manually grasped loop, the latching means attaching the strap to the handcuffs, the strap having a length in the range of sixteen to twenty-four inches; grasping the loop of the strap and walking with and behind the individual to the vehicle; grasping and pulling the free end of a second control strap from within the vehicle, the second control strap having another fixed end secured to the vehicle above and behind the seat backing, the strap normally extending downwardly over the backing toward the rear portion of the support member with the free end of the strap normally resting on the seat, the free end including latching means to attach the free end of the second control strap to the handcuffs; attaching the latching means to the handcuffs; releasing said grasp on the first strap; and, seating the individual in the vehicle on the support member with the second control strap extending from above and behind the seat downwardly over the backing to the handcuffs. The strap is sized to prevent the individual while seated in the seat from working his hands underneath his buttocks and legs to the front of the individual's body.

In another embodiment of my invention I provide a method for a police officer to secure a handcuffed individual in the seat of a vehicle to prevent the individual from working the handcuffs and his hands underneath his legs to the front of his body. The vehicle seat includes an upstanding backing and a horizontally oriented support member forward of the backing and having a rear portion and a forward portion. The method includes the steps in which the officer stands behind the individual and attaches handcuffs to the wrists of the individual's hands positioned behind the individual's back; stands the individual adjacent the vehicle and vehicle seat with the officer positioned behind and grasping the individual; while grasping the standing individual with one hand, grasps with the other hand the free end of a control strap located within the vehicle, the control strap having a fixed end secured to the vehicle above and behind the backing, the strap normally extending from the fixed end downwardly over the backing to the rear portion of the support member with the free end of the strap resting on the seat, the free end including latching means to attach the free end to the handcuffs; attaches with the other hand the latching means to the handcuffs; and, seats the individual in the vehicle on the support member with the control strap extending from above and behind the seat downwardly over the backing to the handcuffs. The strap is sized to prevent the individual while seated in the seat from working his hands underneath his buttocks and legs to the front of the individual's body.

In a further embodiment of my invention, I provide apparatus for restraining a handcuffed prisoner in the seat of a vehicle. The vehicle seat includes an upstanding backing and a horizontally oriented support member forward of the backing and having a rear portion and a forward portion. The apparatus includes an elongate control strap. The strap has a fixed end attached to the vehicle above and behind the backing; and, a free end including latching means adapted to be connected to handcuffs on the hands of an individual sitting in the seat with his hands behind his back. The strap normally extends downwardly over the backing toward the rear portion of the support member with the free end resting on the seat. The strap is sized and attached to the vehicle such that an individual standing outside and next to the vehicle and said seat can bend down and with one hand grasp said free end on said seat, pull the free end from inside the vehicle, and attach the latching means to handcuffs worn behind the back by a prisoner standing adjacent the individual. When the prisoner is seated in the seat with the latching means attached to the handcuffs, the individual is prevented from working his hands forwardly away from the backing and underneath his buttocks and legs to the front of the individual's body.

Figures 1, 2, 3, 4, 5:
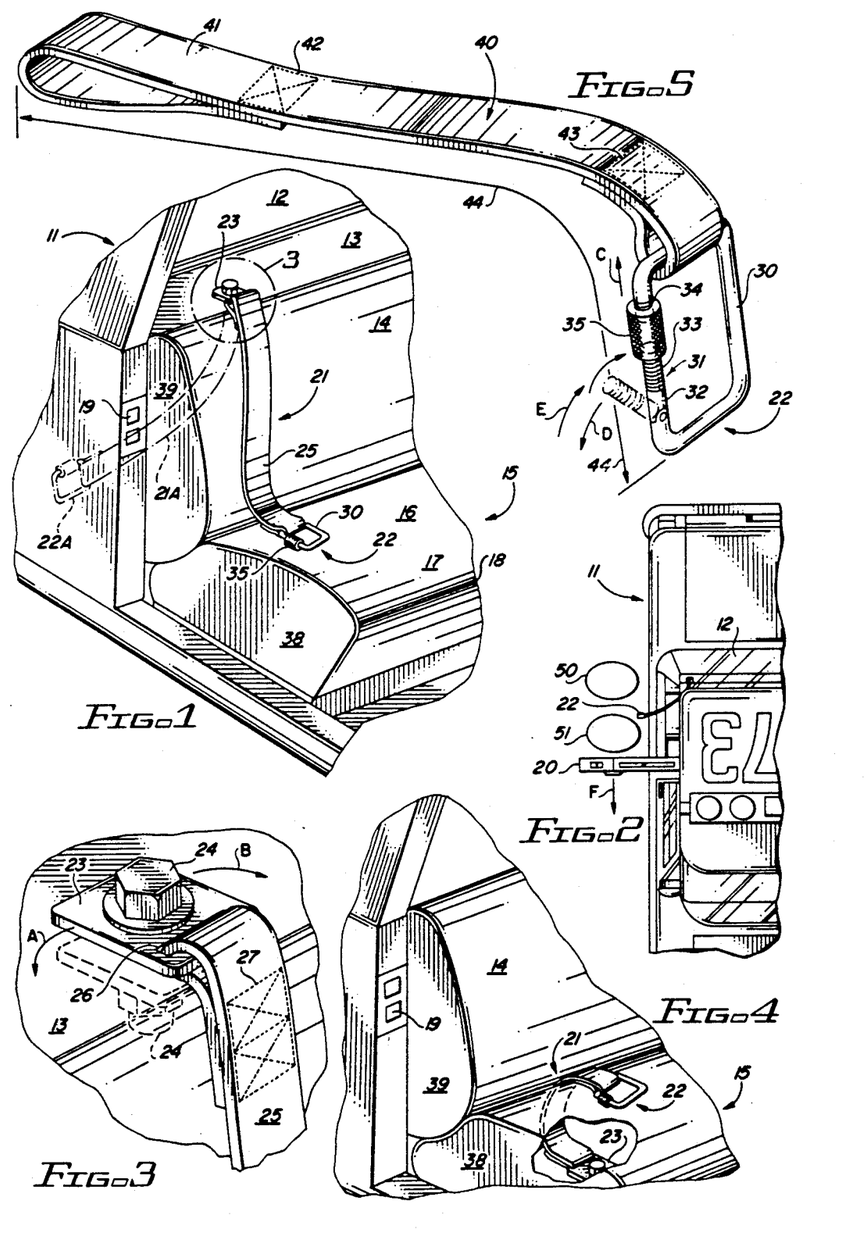
FIG. 1 is a perspective view illustrating a vehicle constructed in accordance with the principles of the invention.
FIG. 2 is a top view of the vehicle of FIG. 1 illustrating the mode of operation of the apparatus of the invention.
FIG. 3 is a perspective view illustrating attachment of the control strap of FIG. 1 to the vehicle.
FIG. 4 is a perspective view illustrating an alternate embodiment of the invention.
FIG. 5 is a perspective view illustrating a control strap constructed in accordance with the invention.

Turning now to the drawings, in which the presently preferred embodiments of the invention are shown for the purpose of illustrating the practice thereof and not by way of limitation of the scope of the invention and in which like elements are indicated by corresponding reference characters throughout the several views, FIGS. 1 to 3 illustrate a vehicle constructed in accordance with the principles of the invention. The vehicle 11 includes rear window 12, horizontal panel 13 immediately beneath window 12, and a back seat including upstanding backing 14 and horizontally oriented support member 15 with a rear portion 16 extending the length of the seat parallel and adjacent backing 14. Member 15 also has a front portion 17 with a leading edge 18 which is ordinarily immediately beneath the knees of an individual sitting on member 15 and against backing 14. Strap 21 includes an upper fixed end 23 attached to panel 13 by bolt 24. Pliable strap 25 loops through rectangular opening 26 and is stitched 27 to itself. Although end 23 is fixed in position against panel 13, it can be rotated about bolt 24 in the manner indicated by arrows A and B. The free end 22 of strap 21 comprises a latch including a U-shaped member 30. A finger 31 is pivotally attached to member 30 at one end 32. The other end 33 of finger 31 is externally threaded. Portion 34 of member 30 is also externally threaded and carries knurled internally threaded member 35. In use, member 35 is threaded upwardly onto portion 34 and off of finger 31 such that finger 31 can be pivoted in the direction of arrow D. Member 30 is fit around the chain interconnecting the cuffs of a pair of handcuffs. Finger 31 is then pivoted in the direction of arrow E and member 35 is partially threaded onto end 33 as illustrated in FIG. 5. The latch comprising the free end 22 of strap 21 can therefore be operated with a single hand. In the practice of the invention it is not necessary that the latch be operable with a single hand; two hands can be utilized. It is, however, preferred that the latch be operable with a single hand. The dashed lines 21A, 22A in FIG. 1 illustrate how free end 22 of strap 21 extends to a point outside vehicle 11 when free end 22 is manually grasped and pulled out from within vehicle 11 by an individual standing adjacent vehicle 11 and adjacent the ends 38 and 39 of support member 15 and backing 14, respectively.

FIG. 5 illustrates an alternate embodiment of the invention including a free end 22 and a loop end 41. The loop end 41 is sized to receive the hand or fingers of an individual. Stitching 42 and 43 is used to form loop 41 and to secure pliable strap 40 to free end 22 in the manner indicated in FIG. 5. The length, indicated by arrows 44, is preferably in the range of twelve to twenty-four inches when the strap is utilized to control a prisoner walking in front of a police officer. When the strap of FIG. 5 is utilized as a hobble, it is approximately four feet long. When used as a hobble, loop 41 is sized to fit over the feet and around the ankles of a prisoner. Free end 22 is attached to the handcuffs, preferably to the chain interconnecting the cuffs, of a prisoner.

Utilization of the method and apparatus of the invention can be explained with reference to FIG. 2. After a police officer arrests a suspect, he stands behind the suspect in conventional fashion and handcuffs the wrists of the suspect behind the suspect's back. The officer then attaches the latch comprising the free end of strap 40 to the handcuffs on the suspect. The latch is preferably attached to the chain interconnecting the cuffs on each wrist of the suspect. The length 44 of the strap is preferably twelve to twenty-four inches. The officer puts one hand through loop 41 and walks behind the suspect as the suspect is directed to vehicle 11. Strap 40 enables the officer to more readily control the suspect. Strap 40 puts a small amount of distance between the officer and suspect and gives the officer more time to react to a sudden movement by the suspect. Further, when the officer is holding strap 40 he can quite readily kick a suspect in the back of the suspect's legs and force the suspect to the ground if he should become unruly. When the officer 50 and suspect 41 arrive at the vehicle 11, the officer stands the suspect 41 in front of him as illustrated in FIG. 2. In FIG. 2, both the officer and suspect 51 are facing forward looking in the direction of arrow F. In this position, the officer 50 is in a superior position to maintain control of the suspect. While holding onto loop 41 of strap 40 with one hand, the officer reaches into vehicle 11 with the other hand and grasps strap 25 first and pulls it outwardly from the car to slide his hand along strap 25 to free end 22. The officer can, alternatively, simply initially grasp free end 22 and lift it from the back seat. Initially grasping strap 25 intermediate ends 22 and 23 and running the hand therealong to end 22 requires the officer to bend down a lesser amount, which makes the officer less vulnerable while he reaches inside vehicle 11 to grasp free end 22. The officer pulls with one hand free end 22 from within the car to the position shown in FIG. 2. He then uses his hand to latch free end 22 onto the handcuffs of the suspect. The operation of the latching mechanism of free end 22 was earlier described. After free end 22 of strap 25 is attached to the suspect's handcuffs, the suspect is told to slide into the back seat of vehicle 11. The officer releases his grasp on loop 41 when the suspect begins to enter the back seat of vehicle 11. If desired, free end 22 of strap 40 can be removed from the suspect's handcuffs before the suspect is seated on support member 15. Once the suspect is seated with his back resting against backing 14, strap 25 extends down over backing 14 in the manner indicated in FIG. 1. Free end 22 is attached to the suspect's handcuffs. Strap 25 prevents a seated suspect from working his hands and handcuffs underneath his buttocks and legs to the front of his body. If a suspect attempts to pull his hands underneath his buttocks, he pulls strap 25 against his back and buttocks. Consequently, the strap 21 inhibits any movement of the hands of a suspect forwardly under his buttocks away from backing 14. If strap 25 is too long, then a suspect can, when free end 22 is attached to the suspect's handcuffs and the suspect is seated on member 15 and against backing 14, work his hands beneath his buttocks and legs to the front of his body. While the length of strap 25 (not including ends 22 and 23) may vary depending on the height of backing 14 and on the point at which fixed end 23 is attached to a vehicle, strap 25 is currently normally 30" to 38" long, preferably 32" to 36" long, in most vehicles. Regardless of the length of strap 25, end 25 must be attached to vehicle 11 at a point near enough to door 20 which permits end 22 to be moved from within the vehicle to be snapped onto the handcuffs of a suspect 51 who is standing adjacent vehicle 11 and is near ends 38 and 39 of the seat of the vehicle.

FIG. 4 illustrates an alternate embodiment of the invention in which fixed end 23 is positioned beneath member 15.

When, in FIG. 5, the length 44 of the strap is in the range of twelve to twenty-four inches, the strap is utilized by an officer to control a prisoner in the manner earlier described. One reason the strap of FIG. 5 gives the officer more control over a prisoner is that strap 40 and loop 41 are pliable. If loop 41 were not pliable, a prisoner normally would be able to break away more quickly. This is, for example, the reason that a prisoner is able to break the hold of an officer on the belt of a suspect. While a belt is somewhat flexible, when a prisoner twists it is difficult to maintain a grasp on the belt. In contrast, when an officer is rasping pliable loop 41, the twisting of a prisoner will normally not cause the officer to lose his grasp.

Figure 6:
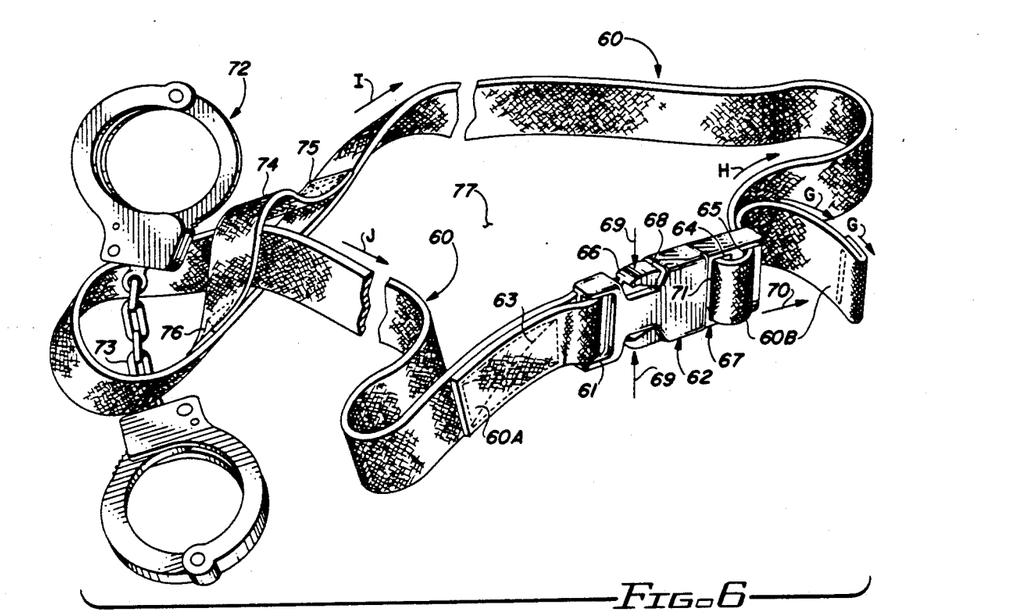
FIG. 6 is a perspective view illustrating another restraining strap assembly constructed in accordance with the invention.
Figure 8:
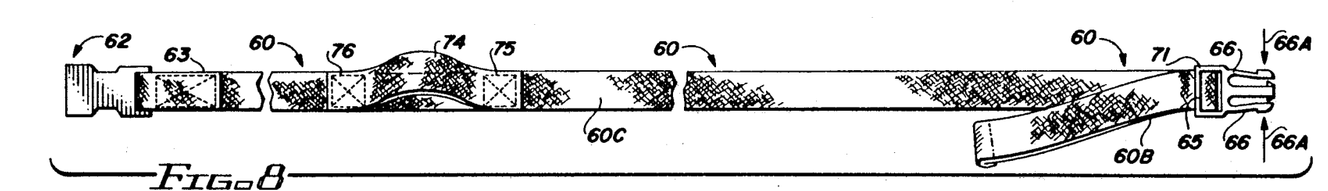
FIG. 8 is a top view of the restraining strap assembly of FIG. 6.

Another restraining strap assembly constructed in accordance with the principles of the invention is illustrated in FIGS. 6 and 8 and includes elongate strap 60 having a first end 60A which is passed through opening 61 of tongue housing or sleeve 62 and is folded against and stitched 63 to strap 60. End 60B is threaded through friction fit openings 64 and 65 formed in tongue assembly 67. Openings 64 and 65 are shaped and dimensioned such that strap 60 and end 60B can not, however, be readily pulled and slid through openings 64 and 65 in the direction indicated by arrows G. End 60B can not, however, be readily pulled and slid through openings 64 and 65 in the direction of arrow H. Resilient tangs 66 are forced inwardly in the directions indicated by arrows 66A when tangs 66 are inserted in and initially contact aperture 68 extending through sleeve 62. When the ends of tangs 66 emerge from aperture 68 they snap outwardly to the position illustrated in FIG. 6 such that the tangs 66 are fixedly engaged with sleeve 62. Tangs 66 are removed from sleeve 62 by squeezing tangs 66 inwardly in the directions indicated by arrows 69 in FIG. 6 with the fingers of one hand while grasping, with the other hand, end 71 of tongue assembly 67 and pulling assembly 67 in the direction indicated by arrow 70 in FIG. 6. The center point 60C of elongate strap 60 is intermediate ends 60A and 60B.

The ends of strip 74 are stitched 75, 76 to strap 60 to form a loop through which either sleeve 62 or tongue assembly 67 can be inserted.

In use of the restraining strap assembly of FIGS. 6 and 8, handcuffs 72 are placed on the wrists of an individual. Strap 60 is threaded around handcuff chain 73, tongue assembly 67 or sleeve 62 is passed through the loop formed by strip 74 and strap 60, strap 60 is drawn around the individual's waist, and the assembly 67 is interfit with sleeve 62 in the manner illustrated in FIG. 6. The portions of strap 60 extending from stitching 75 in the direction of arrow I and extending from strip 74 in the direction of arrow J circumscribe the waist (not shown) of the individual, i.e., circumscribe the open area 77 indicated in FIG. 6. Accordingly, when the individual's hands are handcuffed behind his back, portions of strap 60 extend from the handcuffs around his waist to the front of his body and the tongue assembly 67 and sleeve 62 are normally located adjacent the front waist of the individual. When the individual's hands are handcuffed in front of the individual, the strap 60 extends rearwardly around his waist and the tongue assembly 67 and sleeve 62 are normally located over the small of the back of the individual. Once the strap assembly of FIG. 8 is loosely installed around the waist of a handcuffed individual in the manner illustrated in FIG. 6, the strap assembly is readily tightened about the waist by grasping end 60B and pulling end 60B in the direction indicated by arrows G.

Figure 7:
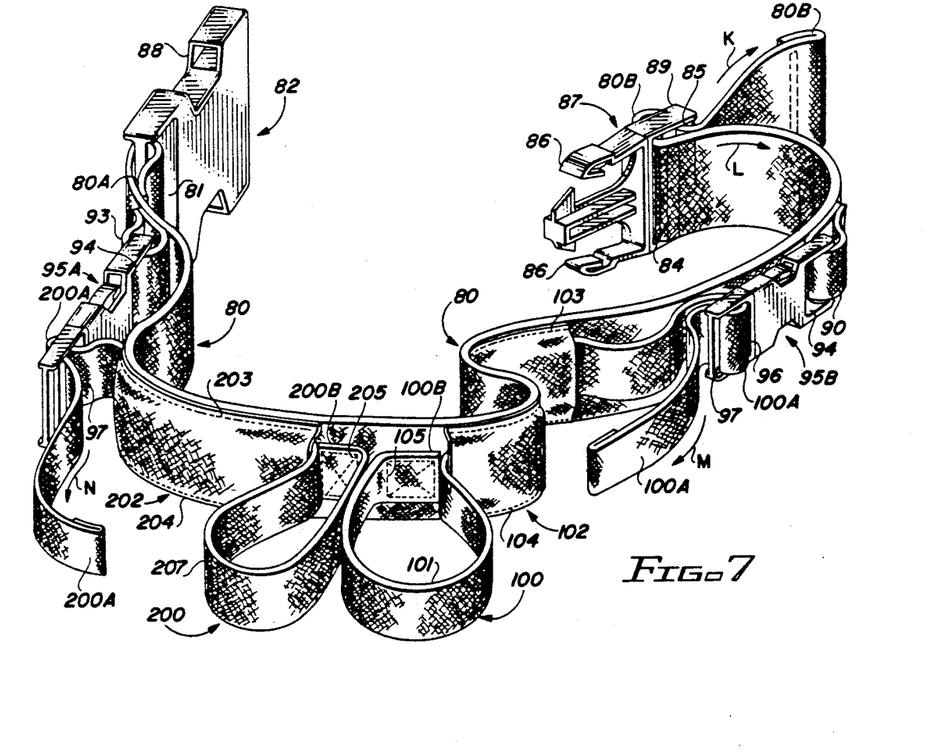
FIG. 7 is a perspective view illustrating still another restraining strap assembly constructed with the invention.
Figure 9:
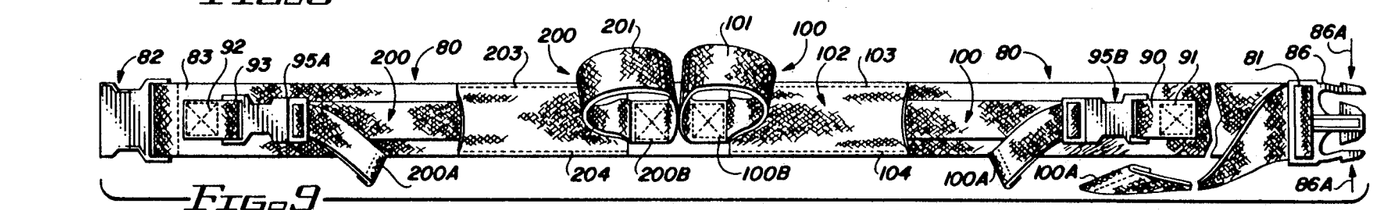
FIG. 9 is a top view of the restraining strap assembly of FIG. 7.

A further restraining strap assembly constructed in accordance with the principles of the invention is illustrated in FIGS. 7 and 9 and includes elongate strap 80 having a first end 80A which is passed through an opening 81 of tongue housing or sleeve 82 and is folded against and stitched 83 to strap 80. End 80B is threaded and slid through friction fit openings 84 and 85 formed in tongue assembly 87. Openings 84 and 85 are shaped and dimensioned such that strap 80 and end 80B thereof can be readily pulled and slid through openings 84 and 85 in the direction indicated by arrow K. End 80B can not, however, be readily pulled through openings 84 and 85 in the direction of arrow L. Resilient tangs 86 are forced inwardly in the directions indicated by arrows 86A when tangs 86 are inserted in and initially contact aperture 88 formed internally of sleeve 82. When the ends of tangs 86 emerge from aperture 88 they snap outwardly to a position similar to that illustrated in FIG. 6 for tangs 66. Tangs 66 are removed from sleeve 82 by squeezing tangs 86 inwardly with the fingers of one hand while grasping, with the other hand, end 89 of tongue assembly 87 and pulling assembly 87 away from sleeve 82 in the direction indicated by arrow K in FIG. 7.

In FIG. 6 the buckle assembly or fastening means includes tongue assembly 67 and sleeve 62. In FIG. 7 the buckle assembly or fastening means includes tongue assembly 87 and sleeve 82. The buckle assembly of FIG. 6 is operated in the same manner as the buckle assembly of FIG. 7.

The ends of strip 93 are stitched 92 to strap 80 to form a loop which passes through aperture 94 to secure buckle 95A to strap 80. The ends of strip 90 are stitched 91 to strap 80 to form a loop which passes through aperture 94 to secure buckle 95B to strap 80. The structure of buckles 95A and 95B is identical.

Elongate pliable fabric strip 102 is stitched 103, 104 along its edges to strap 80 to form a sleeve through which strap 100 may slide intermediate strip 102 and strap 80. End 100A is threaded through friction fit openings 96 and 97 formed in buckle 95B. Openings 96 and 97 are shaped and dimensioned such that strap 100 and end 100A thereof can be readily pulled and slid through openings 96 and 97 in the direction of arrow M. End 100A cannot, however, be readily pulled through openings 96 and 97 in a direction opposite that of the direction indicated by arrow M.

Elongate pliable fabric strip 202 is stitched 203, 204 along its edges to strap 80 to form a sleeve through which strap 200 may slide intermediate strip 202 and strap 80. End 200A is threaded through friction fit openings 96 and 97 formed in buckle 95A. Openings 96 and 97 are shaped and dimensioned such that strap 200 and end 200A thereof can be readily pulled through openings 96 and 97 in the direction of arrow N. End 200A cannot, however, be readily pulled through openings 96 and 97 in a direction opposite that of the direction indicated by arrow N.

Strap 100 extends from end 100B continuously intermediate strip 102 and strap 80 and through buckle 95B. Strap 200 extends from end 200B continuously intermediate strip 202 and strap 80 and through buckle 95A. Strap 100 forms adjustable loop 101. Strap 200 forms adjustable loop 201.

In use of the restraining strap assembly of FIGS. 7 and 9, strap 80 is extended around the waist of an individual and the tongue assembly 87 is then snapped into sleeve 82. End 80B of strap 80 is grasped and pulled in the direction of arrow K to tightened and secure strap 80 around the waist of the individual. Each of the individual's hands is inserted through one of loops 101 and 201 such that the loops encircle the wrists of the individual. End 200A of strap 200 is grasped and pulled in the direction of arrow N to pull strap 200 slidably intermediate strip 202 and strap 80 and to pull end 200A of strap 200 through buckle 95A in the direction of arrow N. Pulling end 200A of strap 200 in the direction of arrow N in the manner described reduces the size of loop 201 and tightens the loop 201 securely about the wrist of the individual. End 100A of strap 100 is grasped and pulled in the direction of arrow M to pull strap 100 slidably intermediate strip 102 and strap 80 and to pull end 100A of strap 100 through buckle 95B in the direction of arrow M. Pulling end 100A of strap 100 in the direction of arrow M in the manner just described reduces the size of loop 101 and tightens the loop 101 securely about the wrist of the individual. As a result when an individual is restrained with the strap assembly of FIGS. 7 and 9, his wrists are snugly encircled and secured by loops 101 and 102 and his hands extend downwardly from the loops 101 and 102 in FIG. 7. It is preferred that buckles 95A, 95B be attached to strap 80 such that when strap 80 is installed on the waist of an individual with loops 101 and 201 adjacent the front waist and stomach of the individual, buckles 95A and 95B are adjacent the individual's back, or are at least adjacent the rear portions of the individual's sides.

Straps 60, 80, 100, 200 and strips 74, 93, 94, 102 and 202 are all preferably fabricated from ballistic nylon like Propex III ™ ballistic cloth. While leather strapping, cotton strapping, metal strapping, or any other desired strapping material can be utilized, ballistic nylon is preferred because it is pliable and relatively non-abrasive and does not tend to cut or bruise the wrists and body of an individual. Ballistic nylon is also extremely tough. While an individual might chew through a leather strap, it is difficult to chew through a strap made from ballistic nylon.

The restraining strap assemblies of FIGS. 6 to 9 are particularly advantageous because they can be quickly installed, are humane, and effectively restrain a prisoner. Prisoners wearing the restraining strap assembly of FIGS. 7 and 9 have thanked the police officer escort because the restraining strap assembly is much more comfortable to wear and causes less bodily injury to the prisoner than does conventional restraint apparatus. The strap assemblies of FIGS. 6 to 9 also permit a certain freedom of movement. A prisoner can slide straps 60 and 80 about his waist without being able to break free of the strap assemblies.

Strap 60 extends from end 60A to end 60B and has a selected length. Strap 60 also has a longitudinal center point which is intermediate ends 60A and 60B. In construction of the strap assembly of FIG. 6, it is important that strip 74 be sewn onto strap 60 at points which are offset from the center point of strap 60 and are intermediate the center point and sleeve 62 or tongue assembly 67. Such off center attachment of strap 74 facilitates the centering of the strap buckle assembly on the stomach or back, as appropriate, of the individual wearing the strap assembly.

FIGS. 10 to 13 disclose still another restraining strap assembly constructed in accordance with the principles of the invention. The body cuff restraining strap assembly of FIGS. 10 to 13 includes rectangular cuff 300 and straps 350, 360, 370, 380 and 390.

Figure 10:
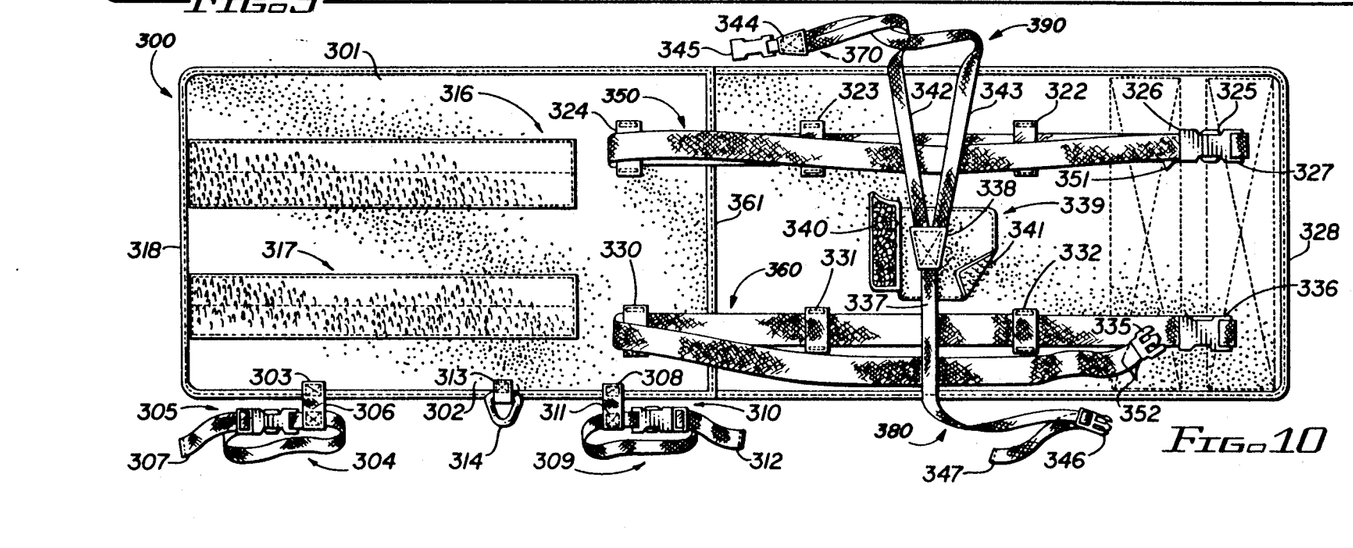
FIG. 10 is a top view of a body cuff arm restraint assembly constructed in accordance with the invention.

The rectangular cuff or pliable piece of material 300 includes an upper edge 301 and lower edge 302. Strap 303 is stitched to the lower edge 302 of cuff 300. Elongate pliable strap 304 is stitched 306 to strap 303. The ends of strap 304 are engaged by buckle assembly 305. Buckle assembly 305 can be a buckle assembly which is equivalent to the seat belt buckle assembly in an automobile or to any other buckle assembly which permits the size of the loop formed by strap 304 to be adjusted. In FIG. 10, the size of the loop formed by strap 304 is reduced by simply pulling on end 307 of strap 304. Buckle assembly 305 preferably is equivalent in structure and function to the tongue assembly 67—sleeve 62 of FIG. 8 and to the tongue assembly 87—sleeve 82 of FIG. 7.

One end of strap 308 is stitched to the lower edge 302 of cuff 300. Elongate pliable strap 309 is stitched 311 to strap 308. The ends of strap 309 are engaged by buckle assembly 310. Buckle assembly 310 can be a buckle assembly which is equivalent to the seat belt buckle assembly in a automobile or to any other buckle assembly which permits the size of the loop formed by strap 309 to be adjusted. In FIG. 10, the size of the loop formed by strap 309 is reduced by simply pulling on end 312 of strap 309. Buckle assembly 310 preferably is equivalent to the tongue assembly 67—sleeve 62 of FIG. 8 and to the tongue assembly 87—sleeve 82 of FIG. 7.

Figures 11, 12, 13:
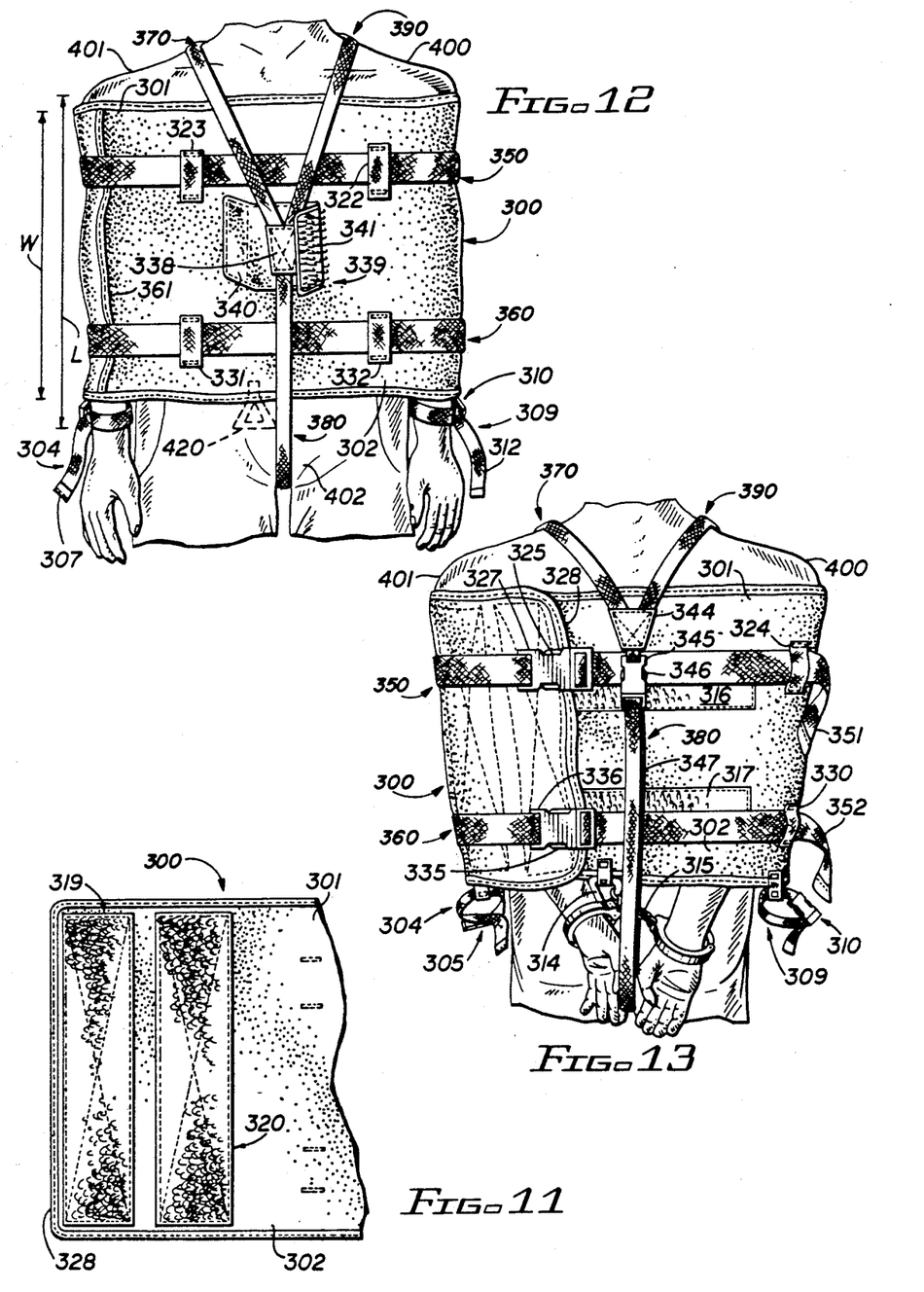

Strap 313 is stitched to the lower edge of cuff 300 and secures eyelet 314 in position adjacent edge 302. As shown in FIG. 13, the chain 315 of a pair of handcuffs or other wrist restraint means is attached to or passes through eyelet 314.

Rectangular "loop" Velcro[200] strips 316 and 317 are attached to the outer surface of cuff 300 and extend inwardly from end 318 of cuff 300. Rectangular "hook" Velcro strips 319 and 320 are attached to the inner surface of cuff 300 and extend parallel to end 328 of cuff 300.

Elongate pliable strap 350 extends slidably through loops 324, 323, and 322. Each loop 322 to 324 is stitched to the outer surface of cuff 300. One end of strap 350 is adjustably connected to tongue assembly 325. The other end of strap 350 is fixedly connected to sleeve assembly 327. Sleeve assembly 336 slidably releasably receives tongue assembly 335.

One end of strap 380 is stitched to cuff 300 and is sandwiched intermediate panel member 338 and pliable rectangular piece of material 339. The stitching that affixes panel member 338, end 337, and material 339 to cuff 300 also affixes the lower ends 342 and 343 of straps 370 and 390 to cuff 300. The upper ends of strap 370 and 390 are stitched to panel member 344. Sleeve assembly 345 is attached to panel member 344 and slidably releasably receives tongue assembly 346 affixed to one end of strap 380. End 347 can be slidably pulled through tongue assembly 346 in conventional fashion in one direction in order to tighten strap 380 when tongue assembly 346 is snapped into sleeve assembly 345. Tongue assembly 346 and sleeve assembly 345 are comparable to the tongue assembly 67 and sleeve 62 of FIG. 8.

Velcro hooks 341 and loops 340 are affixed to the back and front surfaces, respectively, of pliable piece of material 339.

In use of the body cuff of FIGS. 10 to 13, the arms of the individual being restrained are positioned so they extend downwardly from the shoulder of the individual along the body. The arms can extend along the side of the individual, as shown in FIG. 12, can extend behind the back of the individual, as shown in FIG. 13, or, can extend down over the front and stomach of the individual. The rectangular piece of material is wrapped around the torso of the individual such that end 328 overlaps and covers end 318 and Velcro hook strips 319 and 320 are transverse and engage strips 316 and 317. When this is accomplished, loops 322, 323, 331 and 332 are on the front of the restrained individual's body along with panel member 338 and material 339 (See FIG. 12). Alternately, loops 324 and 330 are positioned at the back of the individual's body, along with end 328 (See FIG. 13). Tongue assembly 325 is brought around the left side of the individual, clipped into sleeve assembly 327, and end 351 is slidably pulled through tongue assembly 325 to tighten strap 350 and press cuff 300 against the arms and body of the restrained individual in the manner illustrated in FIGS. 12 and 13. Tongue assembly 335 is brought around the left side of the individual, slipped into sleeve assembly 336, and end 352 is slidably pulled through tongue assembly 335 to tighten strap 360 and press cuff 300 against the arms and body of the restrained individual in the manner illustrated in FIGS. 12 and 13. Straps 370 and 390 are placed over the shoulders of the restrained individual in the manner illustrated in FIGS. 12 and 13. Strap 370 extends over the right shoulder 401 and strap 390 extend over the left shoulder 400. Strap 380 extends from the front of the restrained individual, through the individual's crotch 402, and adjacent the back of the individual and tongue assembly 346 is snapped into sleeve assembly 345. After assembly 346 is snapped into assembly 345, end 347 is pulled through tongue assembly 346 to tighten strap 300 snugly to the crotch 402.

In FIG. 12, the wrists of the restrained individual are secured by placing the loops formed by straps 304 and 309 over the right and left wrists, respectively, and by pulling on ends 307 and 312 to tighten the loops about the wrists. An alternate method of securing the wrists of the restrained individual in a position adjacent lower edge 302 is by engaging the wrists with a pair of handcuffs secured in position by eyelet 314. If desired, an eyelet 314 can be secured to edge 302 in the manner indicated by ghost outlines 420. This would permit the restrained individual's hands to be handcuffed in a position at the front waist of the individual. Straps 304 and 309 can be positioned at any desired location along edge 302.

The body restraint apparatus of FIGS. 10 to 13 has several important advantages. First, the "wrap around" method of installing the apparatus on an individual enables cuff 300 to be quickly positioned on the torso of an individual who is resisting arrest or who otherwise needs to be restrained. Second, the ability to quickly attach and secure straps 350, 360, 370, 380, and 390 also facilitates the rapid use of the body restraint apparatus. The apparatus of the invention is markedly easier to install than a strait jacket. Third, the restraint apparatus of FIGS. 10 to 13 is humane. An individual restrained in the apparatus of the invention is less likely to injure himself or to be injured while the apparatus is being utilized. Fourth, the wrap around construction of cuff 300 combined with straps 350, 360, 370, 380, and 390 makes it very difficult for an individual to escape from the apparatus. An attempt by the individual to pull downwardly on edge 302 is resisted in part by straps 370 and 390 anchored to panel member 338. Pulling down on edge 302 tends to produce undesirable pressure on the crotch 402 and shoulders 400 and 401. Fifth, securing the wrists of the restrained individual adjacent lower edge 302, while being humane and relatively comfortable to the individual, makes it very difficult for the individual to attempt to pull his arms up between cuff 300 and the individual's body. Sixth, the quick release buckle units utilized to releasably interconnect the ends of straps 350 and 360 and to interconnect the end of strap 380 with the ends of straps 370 and 390 makes it an unusually simple matter to remove cuff 300 from a restrained individual. Seventh, installation of the restraint apparatus of FIGS. 10 to 13 normally takes less strength than many prior art restraint devices, particularly strait-jackets.

Means other than Velcro® strips 316, 317, 319, 320 can be utilized to releasably interconnect ends 328 and 318. For example, snaps or a buckle system could be utilized. Velcro is presently preferred because of the speed with which cuff 300 can be wrapped around or removed from an individual.

In FIGS. 12 and 13, straps 304, 309, 380, 350 and 360 are shown after ends 307, 312, 347, 351 and 352, respectively, have been pulled to tighten the straps about the upper body of the restrained individual.

In FIG. 12, loops 340 can be pulled over and pressed against hooks 341 to cover panel member 338.

While the middle portion of strap 350 could be stitched to cuff 300 and loops 322 to 324 eliminated, the loops 322 to 324 enable the position of strap 350 to be slidably adjusted about the body of an individual. The ability to slidably adjust the position of strap 350 (and strap 360) is advantageous because a police officer or other person utilizing the restraint apparatus of FIGS. 10 to 13 can position sleeve assemblies 327 and 336 at any desired position on the back (or the front) of a restrained individual. The slidability of straps 350 and 360 is an important feature because when the restrained individual is putting up resistance, it may be easier, for example, to interconnect buckle assembly 327 and tongue assembly 325 at one location of the individual's torso than at another location. For instance, if the restrained individual is on his back and is refusing to roll over onto his stomach after cuff 300 has been wrapped around his body, strap 350 can be slid through loops 322 to 324 to permit assemblies 325 and 327 to be interconnected on the chest of the individual. Once the restraint apparatus is fully installed on the individual, the position of assemblies 327 and 325 can then, if desired, be adjusted to be at the back of the restrained individual by loosening end 351 in assembly 325, pulling on strap 350 to slide it around the torso of the individual and to move the interconnected assemblies 325 and 327 from the chest to the back of the individual, and by pulling on end 351 to again tighten the strap 350 about the torso of the individual. Consequently, the adaptability of the restraint apparatus of the invention is an important feature of the invention.

If desired, the apparatus of FIGS. 10 to 13 can be put on an individual backwards, that is, with panel member positioned against the back of the individual and with sleeve assemblies 327 and 336 positioned on the chest and stomach of the individual. Tongue assembly 346 would also be adjacent the chest of the individual in such a "backward" installation of the apparatus.

As would be appreciated by those of skill in the art, the length of cuff 300 can be adapted so it wraps around an individual more than once before straps 350, 360, 370, 380, and 390 are tightly secured about the individual.

In FIG. 12, the length of the restrained individual's arms is indicated by arrows L. Cuff 300 is wide enough to extend over substantially the entire length of the arms, where each arm extends from the wrist of the individual to the shoulder. Cuff 300 will normally, in extending over substantially the entire length, indicated by arrow L, of the arm cover at least sixty-six percent of the length L. The width of cuff 300 is indicated by arrow W in FIG. 12. If desired air openings or other openings can be formed through cuff 300.

Having described my invention in such terms as to enable those skilled in the art to understand and practice it, and having identified the presently preferred embodiments thereof, I claim:

1. A humane readily applied restraining strap assembly for an individual, said restraining strap assembly including
   (a) an elongate pliable piece of material shaped and dimensioned to, when the arms of an individual are positioned to extend downwardly from the shoulders along the body of the individual
      (i) wrap completely around the individual in overlapping relationship, and
      (ii) cover substantially the entire length of each arm intermediate the wrist and upper portion of the arm,
   said piece of material including
      (iii) an upper edge extending over the chest and upper back of the individual when said strap assembly is worn by the individual, and
      (iv) a lower edge extending over the waist and lower back of the individual when said strap assembly is worn by the individual;
   (b) a first pliable strap shaped and dimensioned to extend, when said piece of material is wrapped completely around the individual in overlapping relationship, around the individual and the piece of material to press said piece of material against the individual's arms, said strap including
      (i) first and second ends, and
      (ii) fastening means for releasably interconnecting said first and second ends; and,
   (c) loop means attached to said piece of material for slidably securing said first strap adjacent said piece of material and permitting the position of said first and second ends and of said fastening means with respect to said piece of material to be adjusted by sliding at least a portion of said first strap through said loop means and over said piece of material.

2. The restraining strap assembly of claim 1, including second strap means attached to said piece of material and shaped and dimensioned to completely circumscribe, when said piece of material is wrapped completely around the individual in overlapping relationship, the upper body of the individual by extending over at least one shoulder of and through the crotch of the individual.

3. The strap assembly of claim 1 including attachment means attached to said lower edge of said piece of material for securing the wrists of the individual adjacent said lower edge.

4. The strap assembly of claim 3 including an elongate pliable second strap
   (a) including first and second free ends;
   (b) fixedly attached intermediate said first and second ends of said second strap to said piece of material at the front of the individual when said piece of material is wrapped completely around the individual in overlapping relationship;

(c) shaped and dimensioned to completely circumscribe, when said piece of material is wrapped completely around the individual in overlapping relationship, the upper body of the individual by extending over at least one shoulder of and through the crotch of the individual; and, (d) including fastening means for releasably interconnecting said first and second free ends of said second strap at a location adjacent the upper back of the individual.

5. The strap assembly of claim 4 wherein said attachment means comprises a pair of handcuffs interconnected by chain means and attached to said piece of material such that when (a) said piece of material is wrapped completely around the individual in overlapping relationship; and, (b) said second strap circumscribes the upper body of the individual;

said chain means is sandwiched intermediate said second strap and the body of the individual.

6. A humane readily applied restraining strap assembly for an individual, said restraining strap assembly including (a) an elongate pliable piece of material shaped and dimensioned to, when the arms of an individual are positioned to extend downwardly from the shoulders along the body of the individual
  (i) wrap completely around the individual in overlapping relationship, and
  (ii) cover substantially the entire length of each arm intermediate the wrist and upper portion of the arm,
  said piece of material including
  (iii) an upper edge extending over the chest and upper back of the individual when said strap assembly is worn by the individual, and
  (iv) a lower edge extending over the waist and lower back of the individual when said strap assembly is worn by the individual;

(b) a first pliable strap shaped and dimensioned to extend, when said piece of material is wrapped completely around the individual in overlapping relationship, around the individual and the piece of material to press said piece of material against the individual's arms, said strap including
  (i) first and second ends, and
  (ii) fastening means for releasably interconnecting said first and second ends; and, (c) attachment means attached to said piece of material for securing said first strap adjacent said piece of material;

(d) an elongate pliable second strap
  (i) including first and second free ends,
  (ii) fixedly attached intermediate said first and second ends of said second strap to said piece of material at the front of the individual when said piece of material is wrapped completely around the individual in overlapping relationship,
  (iii) shaped and dimensioned to completely circumscribe, when said piece of material is wrapped completely around the individual in overlapping relationship, the upper body of the individual by extending over at least one shoulder of and though the crotch of the individual, and
  (iv) including fastening means for releasably interconnecting said first and second free ends of said second strap at a location adjacent the back of the individual.

7. The restraining strap assembly of claim 6 wherein said attachment means comprises loop means for slidably securing said first strap adjacent said piece of material and permitting the position of said first and second ends and said fastening means of said first strap with respect to said piece of material to be adjusted by sliding at least a portion of said first strap through said loop means and over said piece of material.

8. The restraining strap assembly of claim 7 including attachment means attached to said lower edge of said piece of material for securing the wrists of the individual adjacent said lower edge.

9. The strap assembly of claim 8 wherein said attachment means comprises a pair of handcuffs interconnected by chain means and attached to said piece of material such that when (a) said piece of material is wrapped completely around the individual in overlapping relationship; and, (b) said second strap circumscribes the upper body of the individual;

said chain of said handcuffs is sandwiched intermediate said second strap and the body of the individual.

10. A humane readily applied restraining strap assembly for an individual, said restraining strap assembly including (a) an elongate pliable piece of material shaped and dimensioned to, when he arms of an individual are positioned to extend downwardly from the shoulders along the body of the individual
  (i) wrap completely around the individual in overlapping relationship, and
  (ii) cover substantially the entire length of each arm intermediate the wrist and upper portion of the arm,
  said piece of material including
  (iii) an upper edge extending over the chest and upper back of the individual when said strap assembly is worn by the individual, and
  (iv) a lower edge extending over the waist and lower back of the individual when said strap assembly is worn by the individual;
  (v) a first end having an inner surface and an outer surface, said inner surface facing the individual and said outer surface facing outwardly away from the individual when said piece of material is wrapped around the individual in overlapping relationship.
  (vi) a second end having an inner surface and an outer surface, said inner surface of said second end facing the individual and said outer surface of said second end facing outwardly away from the individual when said piece of material is wrapped around the individual in overlapping relationship, and
  (vii) an elongate axis circumscribing the back and front of the torso of the individual when said piece of material is wrapped around the torso of the individual;

(b) first strap means attached to said piece of material and shaped and dimensioned, when said piece of material is wrapped completely around the individual in overlapping relationship, to extend around the individual and the piece of material to press said piece of material against the individual's arms;
(c) a first elongate strip of hook and loop fastener material attached to said outer surface of said first end and having
  (i) an elongate axis parallel to said elongate axis of said piece of material, and
  (ii) a width dimension perpendicular to said elongate axis of said piece of material and to said elongate axis of said first strip of material;
(d) a second elongate strip of hook and loop fastener material attached to said inner surface of said second end and having
  (i) an elongate axis perpendicular to said elongate axis of said piece of material and to said elongate axis of said first strip of material, and
  (ii) a length dimension perpendicular to said elongate axis of said first strip of material and greater than said width dimension of said first strip of material such that when said piece of material is wrapped completely around the torso of the individual said second end of said piece of material can be laterally displaced a selected distance with respect to said first end while portions of said first and second strips of hook and loop fastener material remain in overlying relationship and can be pressed together to secure said piece of material on the individual.

11. The strap assembly of claim 10 wherein said first strap includes
(a) first and second ends, and
(b) fastening means for releasably interconnecting said first and second ends.

12. The strap assembly of claim 11 including loop means attached to said piece of material for slidably securing said first strap adjacent said piece of material and permitting the position of said first and second ends and said fastening means of said first strap with respect to said piece of material to be adjusted by sliding at least a portion of said first strap through said loop means and over said piece of material.

13. The strap assembly of claim 12 including a second strap
(a) including first and second free ends;
(b) fixedly attached intermediate said first and second ends of said second strap to said piece of material at the front of the individual when said piece of material is wrapped completely around the individual in overlapping relationship;
(c) shaped and dimensioned to completely circumscribe, when said piece of material is wrapped completely around the individual in overlapping relationship, the upper body of the individual by extending over at least one shoulder of and through the crotch of the individual; and,
(d) including fastening means for releasably interconnecting said first and second free ends of said second strap at a location adjacent the upper back of the individual.

14. The strap assembly of claim 13 including attachment means attached to said lower edge of said piece of material for securing the wrists of the individual adjacent said lower edge.

15. The strap assembly of claim 14 wherein said attachment means comprises a pair of handcuffs interconnected by chain means and attached to said piece of material such that when
(a) said piece of material is wrapped completely around the individual in overlapping relationship; and,
(b) said second strap circumscribes the upper body of the individual;
said chain means is sandwiched intermediate said second strap and the body of the individual.

* * * * *